United States Patent [19]

MacDiarmid et al.

[11] Patent Number: 6,090,985
[45] Date of Patent: Jul. 18, 2000

[54] CHIRAL POLYANILINES AND THE SYNTHESIS THEREOF

[75] Inventors: Alan G. MacDiarmid, Drexel Hill, Pa.; Leon A. P. Kane-Maguire, Austinmer, Australia; Weigong Zheng, San Francisco, Calif.; Gordon G. Wallace, Gwynneville; Ian D. Norris, Figtree, both of Australia

[73] Assignee: The Trustees of the University of Pennsylvania, Philadelphia, Pa.

[21] Appl. No.: 09/230,415

[22] PCT Filed: Jul. 25, 1997

[86] PCT No.: PCT/US97/13304

§ 371 Date: Jun. 28, 1999

§ 102(e) Date: Jun. 28, 1999

[87] PCT Pub. No.: WO98/04514

PCT Pub. Date: Feb. 5, 1998

Related U.S. Application Data

[60] Provisional application No. 60/022,694, Jul. 26, 1996.

[51] Int. Cl.$^7$ .................................................. C07C 211/00
[52] U.S. Cl. ........................................... 564/434; 564/243
[58] Field of Search ...................... 564/434, 243

[56] References Cited

U.S. PATENT DOCUMENTS

| | | | |
|---|---|---|---|
| 4,904,553 | 2/1990 | Nakajima et al. | 429/213 |
| 4,940,517 | 7/1990 | Wei | 204/78 |
| 5,276,112 | 1/1994 | MacDiarmid et al. | 525/540 |
| 5,436,317 | 7/1995 | Järvinen et al. | 528/422 |

OTHER PUBLICATIONS

Masters et al Syn Met., 41–43, 715 (1991).
Majidi et al, Polymer, 35 3113 (1994.
Delabouglise et al., *Synth. Metals*, 1990, 39, 117.
Kotkar et al., "Towards Chiral Metals. Synthesis of Chiral Conducting Polymers from Optically Active Thiophene and Pyrrole Derivatives",*J. Chem. Soc. Chem. Commun.*, 1988, 917–918.
Majidi et al. *"Chemical generation of optically active polyaniline via the doping of emeraldine base with (+)–or(–)–comphorsulfonic acid"*, Polymer, 1995, 36(18), 3597–3599.
Salmon et al., "Chiral Polypyrroles from Optically Active Pyrrole Monomers", *J. Electrochem. Soc.*, 1985, 132(8), 1897–1899.

*Primary Examiner*—Paul J. Killos
*Attorney, Agent, or Firm*—Woodcock Washburn Kurtz Mackiewicz & Norris LLP

[57] ABSTRACT

The present invention generally describes novel chiral polyanilines in their doped (protonated) forms and novel methods for their chemical synthesis comprising polymerizing an aniline monomer in the presence of a chiral dopant acid, an oxidizing agent, and, optionally, a substrate, and their conversion by treatment with a base to novel chiral polyanilines in their de-doped base forms. The novel chiral polyanilines of the present invention may be used as electrodes for asymmetric synthesis, as biological sensors and as separation materials in pharmaceutical applications.

16 Claims, 8 Drawing Sheets

CHIRAL POLYANILINES AND THE SYNTHESIS THEREOF

RELATED APPLICATIONS

This application claims priority to U.S. Provisional Patent Application No. 60/022,694, filed Jul. 26, 1996, the disclosure of which is hereby incorporated by reference herein in its entirety.

GOVERNMENT SUPPORT

Portions of the technology disclosed herein were supported by the Australian Research Council Grant Nos. A 29602071 and A 29530422, by the Australian Bilateral Science and Technology Collaboration Program Grant No. 95/4345, and by NIST/ATP 1993-01-0149.

FIELD OF THE INVENTION

The present invention generally describes novel chiral polyanilines and novel methods of chemically synthesizing chiral polyanilines.

BACKGROUND OF THE INVENTION

Chirality and the associated optical activity is an important property of many organic and biological compounds. A molecule that can exist as two mirror images which are not superimposable on each other are called chiral. Although molecular chirality has been known for a long time, chiral conducting polymers have only recently been reported. Some chiral conducting polymers, such as chiral polythiophene (Salmon et al, *J. Electrochem. Soc.*, 132, 1897 (1985)), chiral polypyrrole with an amino acid substituted on the 3-position (Kotkar et al, *J. Chem. Soc. Chem. Commen.*, 917 (1988)), and electrochemically polymerized chiral N-substituted polypyrrole (Delabouglise et al, *Synth. Met.*, 39, 117 (1990)), have been described in the art. Chiral polyaniline has been synthesized by the electropolymerization of aniline in the presence of D-camphor sulfonic acid, as described by Majidi et al, *Polymer*, 35, 3113 (1994), and has been synthesized by doping a polyaniline emeraldine base with D- or L-camphor sulfonic acid, as described by Majidi et al, *Polymer*, 36, 3597 (1995).

Polyaniline is the name given to the polymer having the structure, in a completely reduced leucoemeraldine oxidation state, of the general formula:

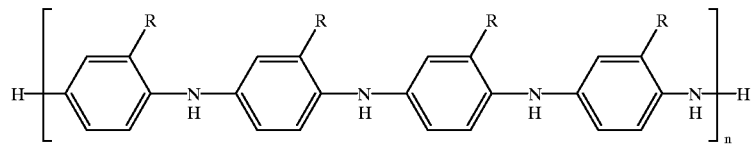

where n is greater than about 25 and where R is a hydrogen atom. Alternatively, R may be a substituent, such as, for example, an organic group, including, for example, $CH_3$, $C_2H_5$, $OCH_3$, $N(CH_3)_2$, an inorganic group, including, for example, F, Cl, Br, I, or a metal chelate group. For all the polyanilines described herein, the appropriate choice of an R group permits a greater range of solubility in a greater number of different types of solvents, which results in increased versatility for processing the polymers and a greater range of chemical properties.

Polyanilines can, in principle, exist in other oxidation states. Masters et al, *Syn. Met.*, 41–43, 715 (1991). For example, polyanilines can exist in the completely oxidized pernigraniline oxidation sate of the general formula:

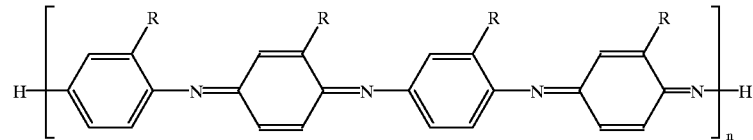

where n is greater than about 25 and where R is a hydrogen atom or a substituent, such as, for example, an organic group, including, for example, $CH_3$, $C_2H_5$, $OCH_3$, $N(CH_3)_2$, an inorganic group, including, for example, F, Cl, Br, I, or a metal chelate group. Polyanilines can also exist in the partially oxidized emeraldine oxidation state of the general formula:

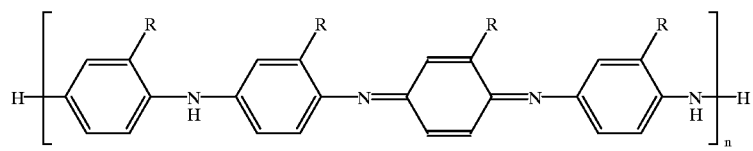

where n is greater than about 25 and where R is a hydrogen atom or a substituent, such as, for example, an organic group, including, for example, $CH_3$, $C_2H_5$, $OCH_3$, $N(CH_3)_2$, an inorganic group, including, for example, F, Cl, Br, I, or a metal chelate group. The emeraldine oxidation state can be protonated by protonic acids, e.g., HA, to give polymers of the general formula:

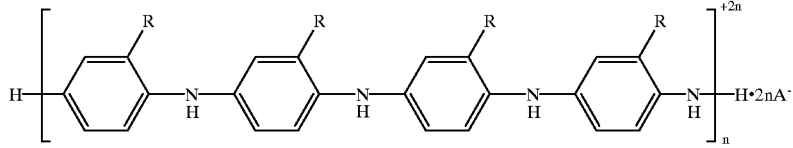

where n is greater than about 25 and where R is a hydrogen atom or a substituent, such as, for example, an organic group, including, for example, $CH_3$, $C_2H_5$, $OCH_3$, $N(CH_3)_2$, an inorganic group, including, for example, F, Cl, Br, I, or a metal chelate group, which exhibit a significant increase in electrical conductivity.

It is well known that the chirality of a molecule induces optical activity. Generally, there are several methods which can be used to characterize the optical activity of a molecule, including optical rotatory dispersion (ORD), circular dichroism (CD) and optical rotation ($[\alpha]_D$). Of these, circular dichroism is the most powerful and sensitive method for the measurement of the chiroptical properties of chiral molecules. For example, electrochemically synthesized chiral polyaniline, as described by Majidi et al, supra, exhibits CD absorption in the UV/Vis region at about 300 nm to 800 nm.

Because chiral conducting polymers offer the unique combination of electronic properties and the character of molecular recognition, there are many important applications for chiral conducting polymers. For example, chiral polymers can be used as chiral electrodes for asymmetric synthesis, as biological sensors, and as chiral separation materials in pharmaceutical applications.

Since previous studies have only focused on the electrochemical polymerization of chiral monomers, there is a need in the art for, among other things, novel methods of chemically synthesizing chiral polyanilines.

SUMMARY OF THE INVENTION

The present invention describes novel methods of synthesizing chiral polyanilines comprising polymerizing an aniline monomer in the presence of an oxidizing agent and a chiral dopant acid to produce the chiral polyaniline.

Another embodiment of the present invention describes methods of synthesizing chiral polyanilines on a substrate comprising polymerizing an aniline monomer in the presence of an oxidizing agent, a chiral dopant acid and a substrate, whereby the chiral polyaniline is deposited on the substrate.

Another embodiment of the present invention describes novel chiral polyanilines produced by polymerizing an aniline monomer in the presence of an oxidizing agent and a chiral dopant acid.

These, as well as other, aspects of the present invention will become apparent from the following detailed description.

DETAILED DESCRIPTION OF THE INVENTION

Figure 1A:
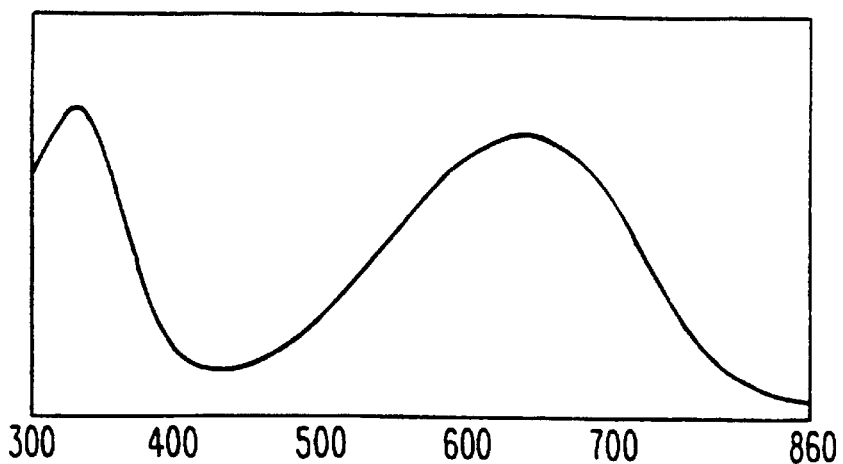
FIG. 1(a) is the UV/Vis spectrum of non-doped polyaniline in an n-methyl pyrrolidinone solution.

As employed throughout the disclosure, the following terms, unless otherwise indicated, shall be understood to have the following meanings.

The term "aniline monomer" refers to compounds of the formula:

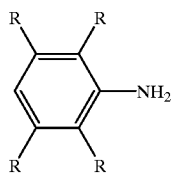

where each R is independently a hydrogen atom or a substituent such as, for example, an organic group, including, for example, $CH_3$, $C_2H_5$, $OCH_3$, $N(CH_3)_2$, an inorganic group, including, for example, F, Cl, Br, I, or a metal chelate group. Preferably, at least three of the four R groups are hydrogen atoms. "Aniline" generally refers to the compound in which each R group is a hydrogen atom. The appropriate choice of an R group permits a greater range of solubility in a greater number of different types of solvents, which results in increased versatility for processing the polymers and a greater range of chemical properties.

In a first embodiment, the present invention describes novel methods of chemically synthesizing chiral polyanilines comprising polymerizing an aniline monomer in the presence of an oxidizing agent and a chiral dopant acid to produce a chiral polyaniline. In particular, the reaction for chemically synthesizing chiral polyanilines may be conducted as follows.

First, an aniline monomer is mixed with a chiral dopant acid. The molar ratio of aniline monomer to chiral dopant acid is generally about 1:8 to about 1:12, preferably about 1:9 to about 1:10. Generally, the molar concentration of aniline monomer is about 0.1075 M and the molar concentration of chiral dopant acid is about 1 M. The reaction is preferably conducted at about room temperature in an aqueous solution, although other polar solvents, such as, for example, methanol or acetonitrile, may be used. The pH of the aqueous solution is generally about 1 to about 4, preferably about 2. The reaction is an instantaneous acid/base reaction that occurs in about 5 to 10 seconds.

Second, an oxidizing agent is dissolved in an aqueous chiral dopant acid solution. The molar ratio of oxidizing agent to chiral dopant acid is generally about 2:1 to about 1:2, preferably about 1:1 to about 1:2, more preferably about 1:1. Generally, the molar concentration of oxidizing agent is about 1.075 M, and the molar concentration of dopant acid is about 1 M. The dissolution of the oxidizing agent in the chiral dopant acid generally occurs at room temperature in about 10 to 20 minutes with magnetic stirring.

Thereafter, the oxidizing agent/chiral dopant acid solution is mixed with the solution resulting from the aniline monomer/chiral dopant acid reaction, which leads to the formation of a dark green precipitate that is a chiral polyaniline salt in the emeraldine oxidation state. The reaction proceeds at room temperature for about 1½ to 2 hours in an aqueous solution, although other solvents which can dissolve the aniline monomer may be used.

The precipitate of the chiral polyaniline salt in the emeraldine oxidation state is removed from the reaction mixture by filtration, washed with water and then washed with a 0.1 M aqueous chiral dopant acid solution until the filtrate is colorless.

In the above reactions, suitable chiral dopant acids include, but are not limited to, (1S)-(+) camphor sulfonic acid, (1R)-(−) camphor sulfonic acid, L-tartaric acid and D-tartaric acid; preferably (1S)-(+) camphor sulfonic acid. Also in the above reactions, suitable oxidizing agents include, for example, ferric chloride hexahydrate ($FeCl_3.6H_2O$), ammonium peroxydisulfate (($NH_4)_2S_2O_8$), $Ce(SO_4)_2$, $KMnO_4$, $KBrO_3$, $K_2Cr_2O_7$, $KIO_3$, $H_2O_2$, $V_2O_5$, $NaVO_3$ and NaClO; preferably ammonium peroxydisulfate.

The chiral polyaniline produced by the above method is in the form of a polyaniline salt in the emeraldine oxidation state. This chiral polyaniline emeraldine salt may be contacted with a base to produce polyaniline emeraldine base. This deprotonation reaction is conducted at room temperature in approximately 250 ml of an aqueous solution at a pH of about 10 to about 11. The deprotonation reaction is allowed to proceed for about 15 hours. Suitable bases for use in the deprotonation reaction include ammonium hydroxide ($NH_4OH$), NaOH, KOH, or any strong organic amine base, such as pyrrolidine. Generally, the base has a molar concentration of about 0.1 M.

Solutions, in dimethyl sulfoxide (DMSO), of the chemically-produced powder of the chiral polyaniline salt in the emeraldine oxidation state, both for the (S)-(+) and (R)-(−)-camphor sulfonic acid forms, had a CD spectrum similar to the CD spectrum previously reported by Majidi et al, supra. For these salts synthesized by chemical doping of polyaniline base in the emeraldine oxidation state with a solution in DMSO of the (S)-(+) and (R)-(−) forms of camphor sulfonic acid.

A second embodiment of the present invention describes methods of synthesizing chiral polyanilines as thin films on a substrate comprising polymerizing an aniline monomer in the presence of an oxidizing agent, a chiral dopant acid and a substrate, whereby the chiral polyaniline is deposited on the substrate.

First, an aniline monomer is mixed with a chiral dopant acid. The molar ratio of aniline monomer to chiral dopant acid is generally about 1:8 to about 1:12, preferably about 1:9 to about 1:10. Generally, the molar concentration of aniline monomer is about 0.1075 M and the molar concentration of chiral dopant acid is about 1 M. The reaction is preferably conducted in an aqueous solution, although other polar solvents, such as methanol or acetonitrile, may be used. The pH of the aqueous solution is about 1 to about 4, preferably about 2. The reaction is an instantaneous acid/base reaction that occurs in about 5 to 10 seconds.

Second, a substrate is immersed in the solution of the aniline monomer and chiral dopant acid. Suitable substrates include, but are not limited to, glass, poly(methyl methacrylate), poly(ethylene phthalate), silicon wafers, and fabric fibers.

Third, an oxidizing agent is dissolved in an aqueous chiral dopant acid solution. The molar ratio of oxidizing agent to chiral dopant acid is generally about 2:1 to about 1:2, preferably about 1:1 to about 1:2, more preferably about 1:1. Generally, the molar concentration of oxidizing agent, such as ammonium persulfate, is about 1.075 M, and the molar concentration of dopant acid is about 1 M. The dissolution occurs at room temperature in about 10 to 20 minutes with magnetic stirring.

Thereafter, the oxidizing agent/chiral dopant acid solution is added to the solution resulting from the reaction of the aniline monomer and chiral dopant acid. The reaction proceeds at room temperature in an aqueous solution, although other solvents which can dissolve the aniline monomer may be used. In about 5 to 10 minutes, a chiral polyaniline thin film will form on the substrate. The thin film is about 800 to 1,000 Å thick. The thickness can be varied by changing the deposition time. The chiral polyaniline film that forms on the substrate is in a pernigraniline oxidation state. Thus, the chiral polyaniline thin film and substrate are immersed in a solution of aniline monomer and chiral dopant acid for about 30 to 40 minutes to reduce any chiral polyaniline in the pernigraniline oxidation state to chiral polyaniline in the emeraldine oxidation state. The chiral polyaniline film on the substrate may be further purified by rinsing with distilled water.

In the above reaction, suitable chiral dopant acids that may be used include, but are not limited to, (1S)-(+) camphor sulfonic acid, (1R)-(−) camphor sulfonic acid, L-tartaric acid and D-tartaric acid; preferably (1S)-(+) camphor sulfonic acid. Suitable oxidizing agents include, for example, ferric chloride hexahydrate ($FeCl_3.6H_2O$), ammonium peroxydisulfate (($NH_4)_2S_2O_8$), $Ce(SO_4)_2$, $KMnO_4$, $KBrO_3$, $K_2Cr_2O_7$, $KIO_3$, $H_2O_2$, $V_2O_5$, $NaVO_3$ and $NaClO$; preferably ammonium peroxydisulfate.

The chiral polyaniline salt thin film on the substrate produced by this method will be in the emeraldine oxidation state. Accordingly, the chiral polyaniline emeraldine salt may be contacted with a base to produce a chiral polyaniline emeraldine base. This deprotonation reaction is conducted at room temperature in about 200 ml of an aqueous solution at a pH of about 11 to about 14. The deprotonation reaction is allowed to proceed for several hours, depending on the amount of polymer that is used. Suitable bases for use in the deprotonation reaction include ammonium hydroxide ($NH_4OH$), NaOH, KOH, or any strong organic amine base, such as pyrrolidine. Generally, the base has a molar concentration of about 1.0 M.

The chiral polyaniline films generated by the methods of the present invention possess characteristic CD bands at about 445 nm that have the same sign as corresponding CD bands for the electrochemically generated films, as described by Majidi et al, supra, although they are somewhat less intense. Unlike the electrochemically generated films, no distinct CD band was observed at about 330 nm and no CD band associated with the localized polaron absorption band (at 820 nm) was observed. These observations indicate that the configuration of the chiral polyaniline films formed electrochemically and by the present methods are different.

In another embodiment, the present invention describes novel chiral polyanilines produced by polymerizing an aniline monomer in the presence of an oxidizing agent and a chiral dopant acid following the methods described in detail above. The chiral polyaniline produced by the methods of the present invention has a different CD spectrum, and consequently a different conformation for its polymer chain, than the chiral polyaniline produced by the electrochemical methods described by Majidi et al, supra.

The novel chiral polyanilines described and synthesized herein may be used, for example, as electrodes for asymmetric synthesis, as biological sensors and as chiral separation materials in pharmaceutical applications.

EXAMPLES

The following examples are presented for purposes of elucidation and not limitation. The examples are not intended, nor are they to be construed, as limiting the scope of the disclosure or claims.

Example 1

Synthesis of Novel Chiral Polyaniline Powder

Aniline (99.5%, Aldrich) was distilled before use. (1S)-(+) camphor-sulfonic acid (98%, Aldrich), (1R)-(−) camphor sulfonic acid (98%, Aldrich), L-tartaric acid (99%, Aldrich), and ammonium peroxydisulfate (99%, Fisher Scientific) were used as received. Glass microscope slides (Finest Fisher) were cleaned by air duster and Kimwipes. The circular dichroism (CD) spectra was recorded by a Jobin-Yvon Dichlograph 6. The UV/Vis spectra was recorded by a Perkin Elmer Lambda 9 UV/Vis/NIR spectrometer. The surface resistance of the thin films was measured by the standard four probe method.

About 2 ml of distilled aniline was added to a 400 ml beaker containing about 200 ml of 1 M aqueous (1S)-(+) camphor sulfonic acid (+HCSA) solution with magnetic stirring for about 15 minutes. About 1.15 g of ammonium peroxydisulfate was dissolved in about a 10 ml solution of 1 M (1S)-(+) camphor sulfonic acid. The solution of ammonium peroxydisulfate was quickly (within about 2 seconds) added, with magnetic stirring, to the beaker containing the 200 ml of aniline/camphor sulfonic acid solution. A dark green precipitate started to form after about 3 minutes. The reaction was allowed to proceed for 1½ hours.

After the reaction was completed, the dark precipitate was collected on a Buchner funnel (7 cm diameter) with a No. 1 Whatman filter paper using a water aspirator. The resulting wet precipitate cake was transferred to a 400 ml beaker and washed with about 400 ml of 0.1 M aqueous (1 S)-(+) camphor sulfonic acid solution. The procedure was repeated (about 5 or 6 times) until the filtrate was colorless. The precipitate was collected on a Buchner funnel and dried by a mechanical pump at room temperature for about 48 hours in a vacuum desiccator. The resulting black dry powder was soluble in chloroform ($CHCl_3$), dimethylacetamide (DMAc), n-methyl pyrrolidinone (NMP) and other common solvents.

Elemental analysis revealed that the sample contained about 62.35% C, about 6.88% N and about 6.12% H. Since camphor sulfonic acid does not contain nitrogen, the percentage of chiral polyaniline in a given weight of the sample was calculated from the result of the nitrogen analysis. In other words, the rest of the weight of the sample would be the weight of the camphor sulfonic acid. From this calculation, the molar ratio of the tetramer unit of emeraldine base (about 0.339 mole) and (1S)-(+) camphor sulfonic acid (about 0.661 mol) in the sample is about 1:2, which indicates that the chiral polyaniline is fully doped by (1 S)-(+) camphor sulfonic acid in the powder form. The chiral polyaniline in the powder form is in the form of an emeraldine salt.

To obtain the base form of the polyaniline, about 0.5 g of the above precipitate was transferred to a 400 ml beaker containing 250 ml of 0.1 M $NH_4OH$ with magnetic stirring for about 15 hours to convert the emeraldine salt to an emeraldine base. The precipitate was collected on a Buchner funnel (7 cm diameter) with a No. 1 Whatman filter paper. At this stage, the dark blue precipitate was washed with about 200 ml of 0.1 M $NH_4OH$ on the funnel. This washing procedure was repeated (about 5 or 6 times) until the filtrate was colorless. Finally, the precipitate was collected on the Buchner funnel after about 15 minutes of suction. The precipitate cake was allowed to partially dry in a vacuum desiccator under a dynamic vacuum for about 24 hours. The partially dried powder was pulverized by a mortar and pestle to a fine powder. The resulting fine powder of emeraldine base was spread on a petri dish (15 cm diameter) and was pumped in a vacuum desiccator for another 48 hours. The resulting dark blue powder of polyaniline emeraldine base was then kept in a screw capped jar for future use.

An elemental analysis was conducted on the dry polyaniline emeraldine base powder. From the C, H, N analysis shown in the table below it is scientifically valid to assume that the polyaniline emeraldine base film prepared in Example 2 below, using the same chemical reagents and method, has the same high degree of chemical purity. It should be noted that the reaction time in Example 1 was about 1½ hours, which provided enough time for the initially generated chiral polyaniline in the pernigraniline oxidation state to convert to the emeraldine oxidation state. In Example 2, the reaction time was only about 5 minutes, such that an additional step was necessary to convert the chiral polyaniline in the initial pernigraniline oxidation state to the emeraldine oxidation state.

TABLE 1

Analysis of Chiral Polyaniline Emeraldine Base Powder ($C_{24}H_{18}N_4$)

|  | Carbon | Hydrogen | Nitrogen | Total |
|---|---|---|---|---|
| Calculated | 79.53 | 5.01 | 15.46 | 100.00 |
| Experimental | 78.51 | 5.70 | 15.15 | 99.36 |

Figure 1B:
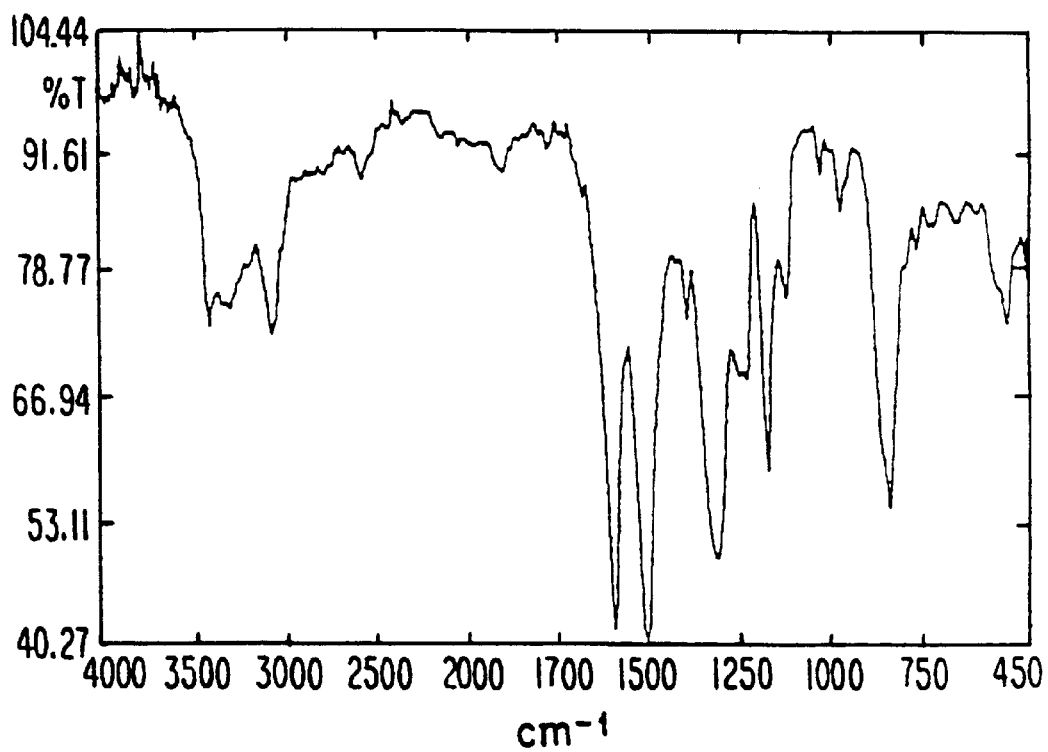
FIG. 1(b) is the diffuse reflectance IR spectrum of non-doped polyaniline powder.

The UV/Vis spectrum (FIG. 1($a$)) of the resulting emeraldine base in n-methyl pyrrolidinone (NMP) solution peaks at about 328 nm and about 635 nm, which is in agreement with previous published values for the non-chiral polyaniline emeraldine base in a NMP solution. Masters et al, supra. The diffuse reflectance (DR) infrared spectrum (FIG. 1($b$)) of the resulting emeraldine base has five principle vibrations at 1592 cm$^{-1}$, 1490 cm$^{-1}$, 1311 cm$^{-1}$, 1165 cm$^{-1}$ and 831 cm$^{-1}$, which are essentially identical to the values of a pure polyaniline emeraldine base synthesized without chiral dopants.

Chiral polyaniline powder using (1R)-(−) camphor sulfonic acid was prepared in a similar manner.

As one skilled in the art would recognize, no CD spectrum would be obtained in the absence of a chiral species or in the presence of equal quantities of the D- and L- forms of the chiral species.

Example 2

Synthesis of In Situ Deposited Novel Chiral Polyaniline Films

Instead of producing a chiral polyaniline powder as in Example 1, thin films of chiral polyaniline on a substrate can be obtained by an in situ "1-dip" deposition method, as described herein.

About 2 ml of distilled aniline was added to a 400 ml beaker containing about 200 ml of 1 M aqueous (1S)-(+) camphor sulfonic acid solution with magnetic stirring for about 15 minutes. Four glass microscope slides were then immersed and placed against the wall of the beaker in the above aniline/camphor sulfonic acid solution. Thereafter, about 1.15 g of ammonium peroxydisulfate was dissolved in a 10 ml solution of 1 M (1S)-(+) camphor sulfonic acid solution. The solution was quickly (within about 1 or 2 seconds) added, with gentle magnetic stirring, to the beaker containing the microscope slides and the 200 ml of the aniline/camphor sulfonic acid solution. A dark green precipitate started to form after about 3 minutes.

After about 5 minutes, the microscope slides were taken out of the solution and rinsed twice with a 0.1 M (1S)-(+) camphor sulfonic acid solution to remove any big particles, unreacted oxidant and monomer from the films. Then the films were immediately immersed in about 200 ml of a 1 M aqueous (1S)-(+) camphor sulfonic acid solution containing about 2 ml of aniline for about 30 minutes to convert the first-formed polyaniline in the pernigraniline oxidation state to the doped polyaniline salt in the emeraldine oxidation state. The films were further rinsed with about 200 ml of 0.1 M aqueous (1S)-(+) camphor sulfonic acid solution to remove excess (1S)-(+) camphor sulfonic acid. The films were then dried by an air gun at room temperature.

Thin films of polyaniline doped with (1R)-(−) camphor sulfonic acid and L-(+) tartaric acid were also prepared in the same manner.

Figure 2A:
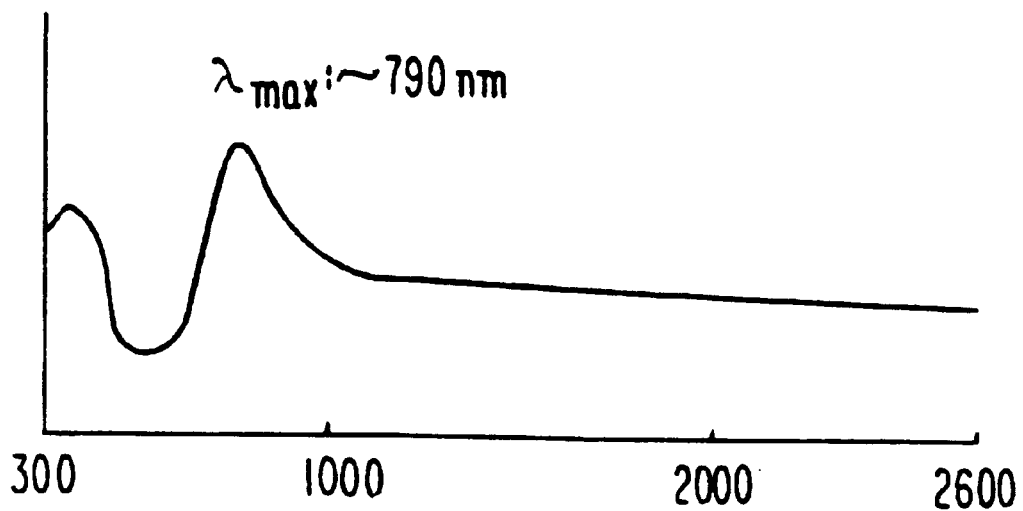
FIG. 2(a) is the UV/Vis spectra of in situ deposited polyaniline thin film doped with (1S)-(+) camphor sulfonic acid.
Figure 2B:
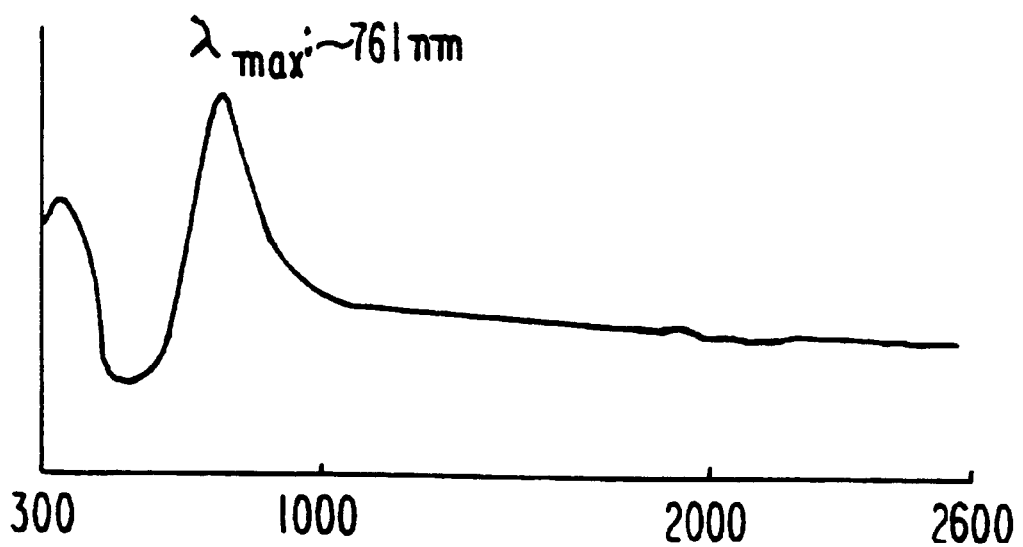
FIG. 2(b) is the UV/Vis spectra of in situ deposited polyaniline thin film doped with (1R)-(−) camphor sulfonic acid.

The UV/Vis spectra of thin films of polyaniline doped with (1S)-(+) camphor sulfonic acid and (1R)-(−) camphorsulfonic acid are shown in FIGS. 2($a$) and 2($b$). The surface resistance of the thin films is about 2.8×10$^4$Ω/□, as measured by the standard four probe method.

Figure 3A:
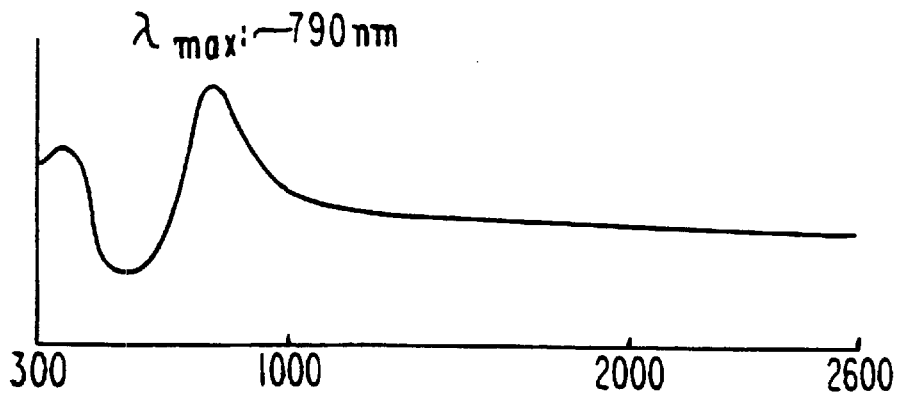
FIG. 3(a) is the UV/Vis spectra of an in situ deposited thin film of polyaniline emeraldine base doped with (1S)-(+) camphor sulfonic acid.
Figure 3B:
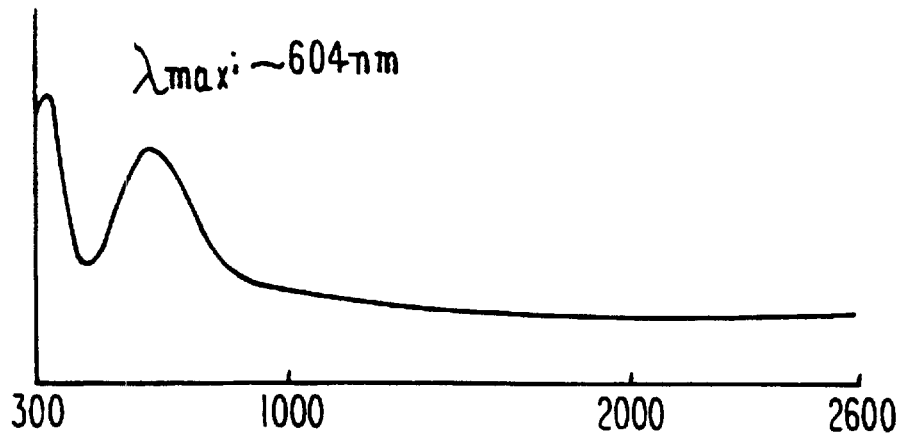
FIG. 3(b) is the UV/Vis spectra of the in situ deposited thin film of polyaniline emeraldine base doped with (1S)-(+) camphor sulfonic acid, after it has been dedoped by aqueous $NH_4OH$.
Figure 3C:
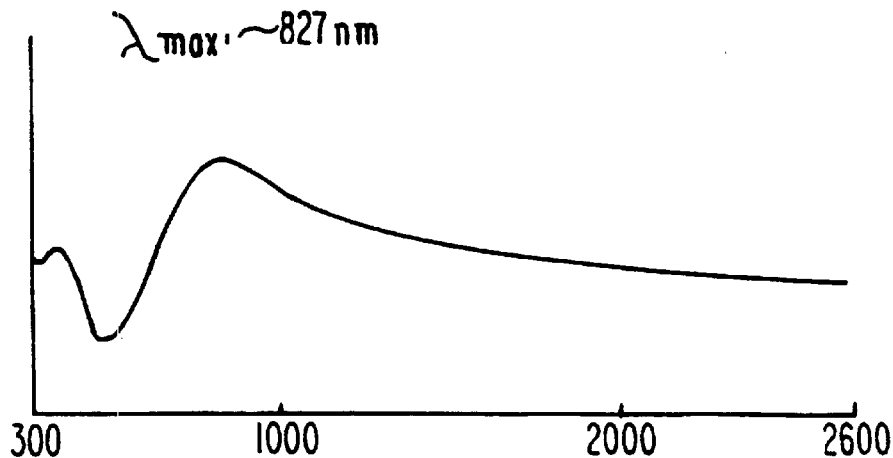
FIG. 3(c) is the UV/Vis spectra of the in situ deposited thin film of the polyaniline emeraldine base doped with (1S)-(+) camphor sulfonic acid, after it has been dedoped by aqueous $NH_4OH$, and after it has been redoped by HCl vapor.

The doped thin films were deprotonated by immersion in a 1 M ammonium hydroxide solution to give the base form of the chiral polyaniline. The resulting blue colored films were also dried by an air gun at room temperature. The UV/Vis spectra of this deprotonated chiral polyaniline base thin films is shown in FIG. 3($b$) is identical to the spectrum of non-chiral polyaniline base films prepared from aniline, oxidant and HCl followed by deprotonation.

Example 3

Circular Dichroism Studies of Novel Chiral Polyaniline Thin Films

Figure 4A:
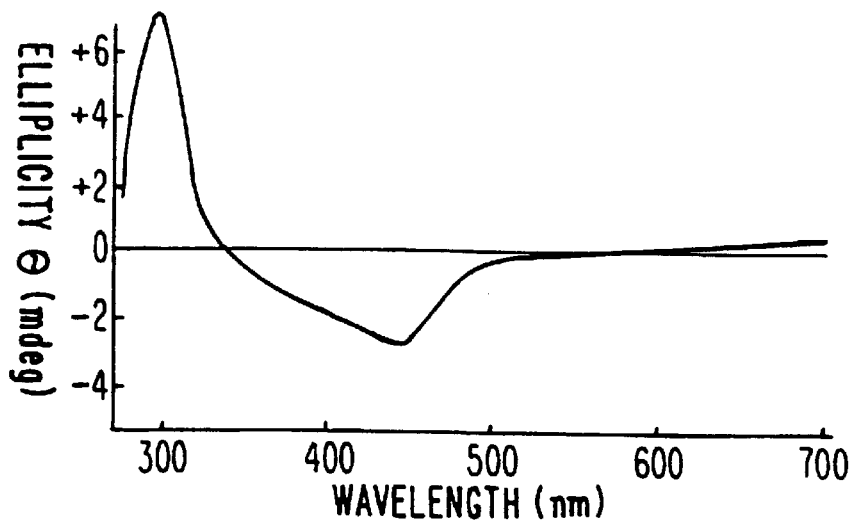
FIG. 4(a) is the CD spectra of an in situ deposited thin film of polyaniline emeraldine base doped with (1S)-(+) camphor sulfonic acid.
Figure 4B:
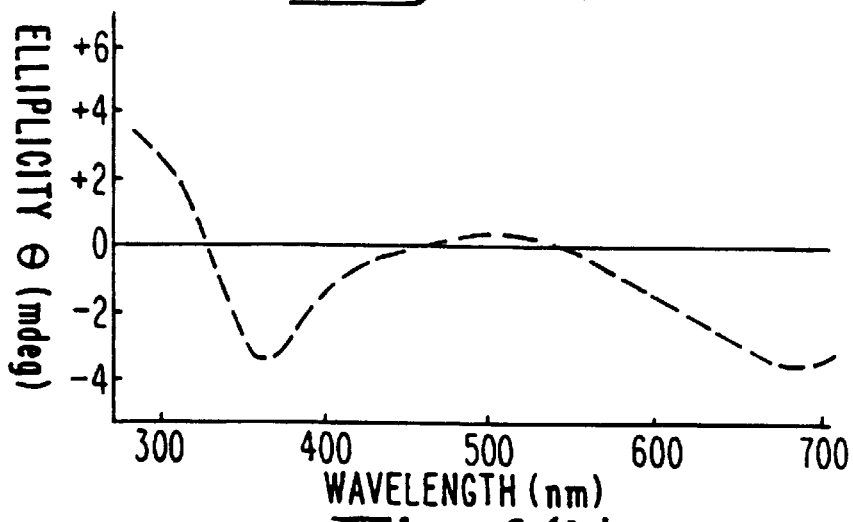
FIG. 4(b) is the CD spectra of the in situ deposited thin film of the polyaniline emeraldine base doped with (1S)-(+) camphor sulfonic acid, after it has been deprotonated by aqueous $NH_4OH$.

As shown in FIG. 4($a$), the CD spectrum of the thin film of chiral polyaniline in the emeraldine oxidation state doped with (1S)-(+) camphor sulfonic acid showed two strong absorption bands in the UV/Vis region. One absorption band is located at about 300 nm with a (+) sign (positive Cotton Effect), which is due to the absorption caused by (1S)-(+) camphor sulfonic acid. The other absorption band has a negative $\lambda_{max}$ at about 450 nm. Since the (1S)-(+) camphor sulfonic acid does not have any absorption in the visible region, the broad CD band at about 450 nM with a negative sign is assigned to the absorption caused by the chiral polyaniline backbone.

It is very important to note that the CD signal still persisted after deprotonation in 1 M aqueous NH$_4$OH, as shown in FIG. 4($b$). The originally strong absorption caused by the (1S)-(+) camphor sulfonic acid at ~300 nm essentially disappears. Moreover, the 450 nm absorption band characteristic of chiral doped polyaniline (which corresponded to the UV/Vis absorption of the doped polyaniline at about 430 to 440 nm) shifts to 370 nm, and instead a new CD band around 520 nm appears. These two CD absorption bands are related to the π–π* peak at about 330 nm and exciton excitation peak at about 600 nm in the UV/Vis spectrum of the in situ deposited non-chiral polyaniline base films prepared from aniline, oxidant and HCl followed by deprotonation. This indicates that the polymer still retained its chiral backbone and optical activity, even after removal of the chiral dopant. This clearly demonstrates that the chiral camphor sulfonic acid caused the polyaniline to become chiral, since the polyaniline remained chiral even after removal of the chiral acid.

Figure 4C:
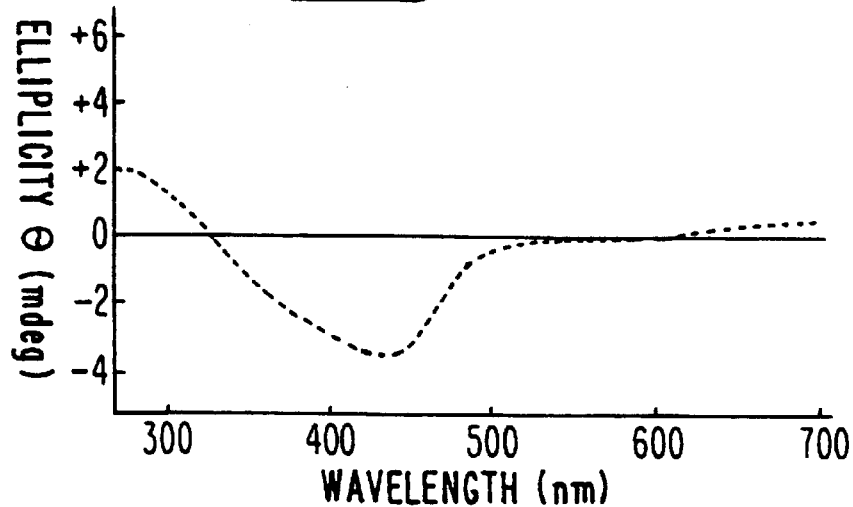
FIG. 4(c) is the CD spectra of the in situ deposited thin film of the polyaniline emeraldine base doped with (1S)-(+) camphor sulfonic acid, after it has been deprotonated by aqueous $NH_4OH$, and after it has been redoped by HCl vapor.

Further experiments showed that when the above thin film was treated by HCl vapor (FIG. 4($c$)), the negative ~450 nm absorption band appeared again showing that the chiral polyaniline backbone had survived on dedoping followed by the re-doping process. The deprotonation and subsequent re-protonation with non-chiral HCl to form a chiral polyaniline salt clearly shows that the chirality is associated only with the polyaniline. The original ~300 nm peak associated with the (1S)-(+) camphor sulfonic acid does not reappear, showing that the observed chirality is not caused by residual camphor sulfonic acid (FIG. 4(c)).

Figure 5:
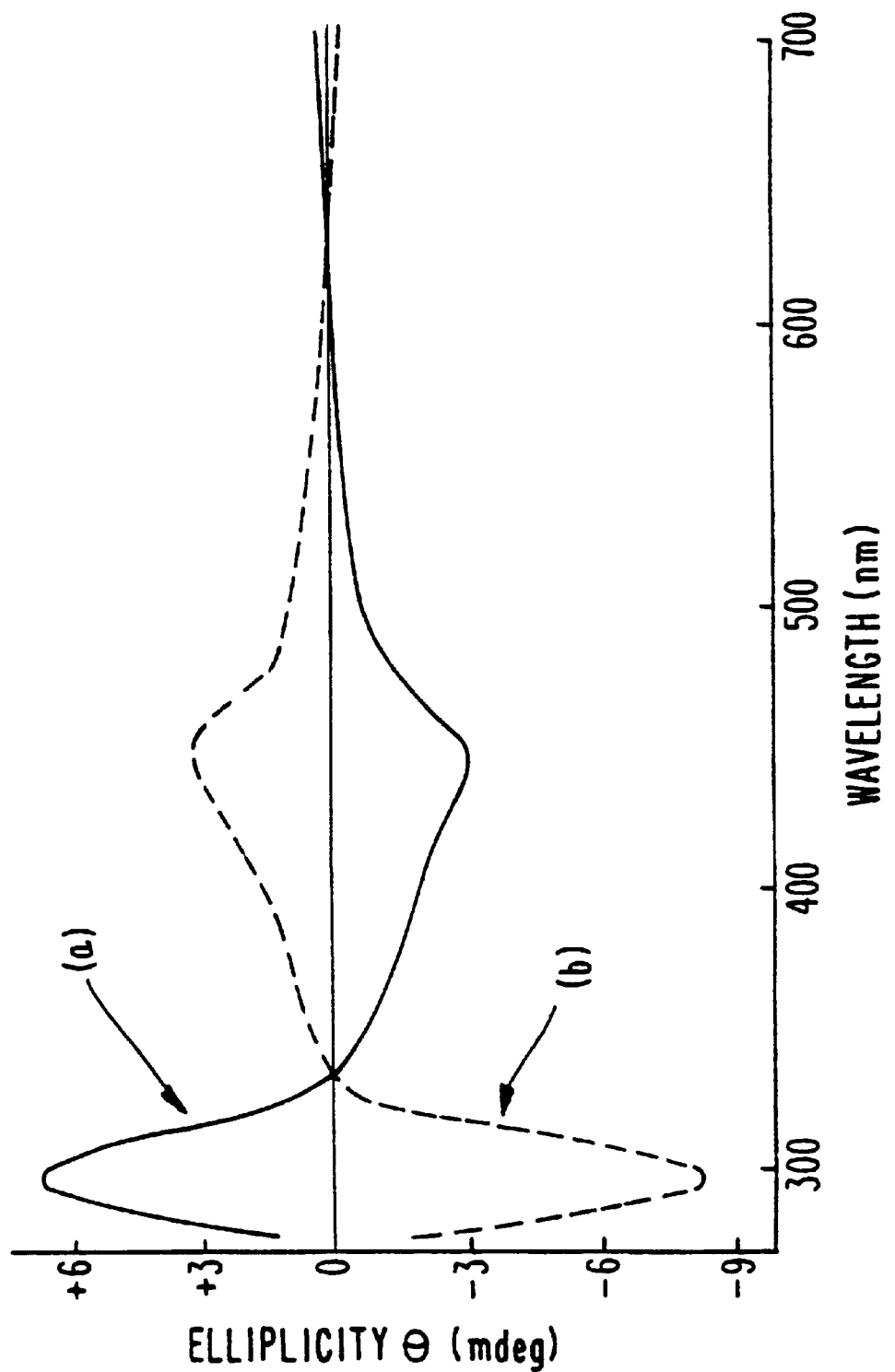
FIG. 5 is (a) the CD spectra of an in situ deposited thin film of polyaniline emeraldine base doped with (1S)-(+) camphor sulfonic acid, and (b) the CD spectra of an in situ deposited thin film of polyaniline emeraldine base doped with (1R)-(−) camphor sulfonic acid.

As shown in FIG. 3, the doping and dedoping of chiral polyaniline can be monitored by UV/Vis spectra. It is important to note that the CD spectra of in situ deposited chiral polyaniline salt films in the emeraldine oxidation state prepared by (1S)-(+) camphor sulfonic acid and (1R)-(−) camphor sulfonic acid are both optically active, with mirror image bands, as shown in FIG. 5. This shows that the chirality of the polyaniline backbone is enantioselective in the presence of (+) or (−) camphor sulfonic acid, i.e., the polymer chains can adapt either a left or right handed helical screw depending on the chirality of the camphor sulfonic acid used to induce chirality in the polymer.

Figure 6:
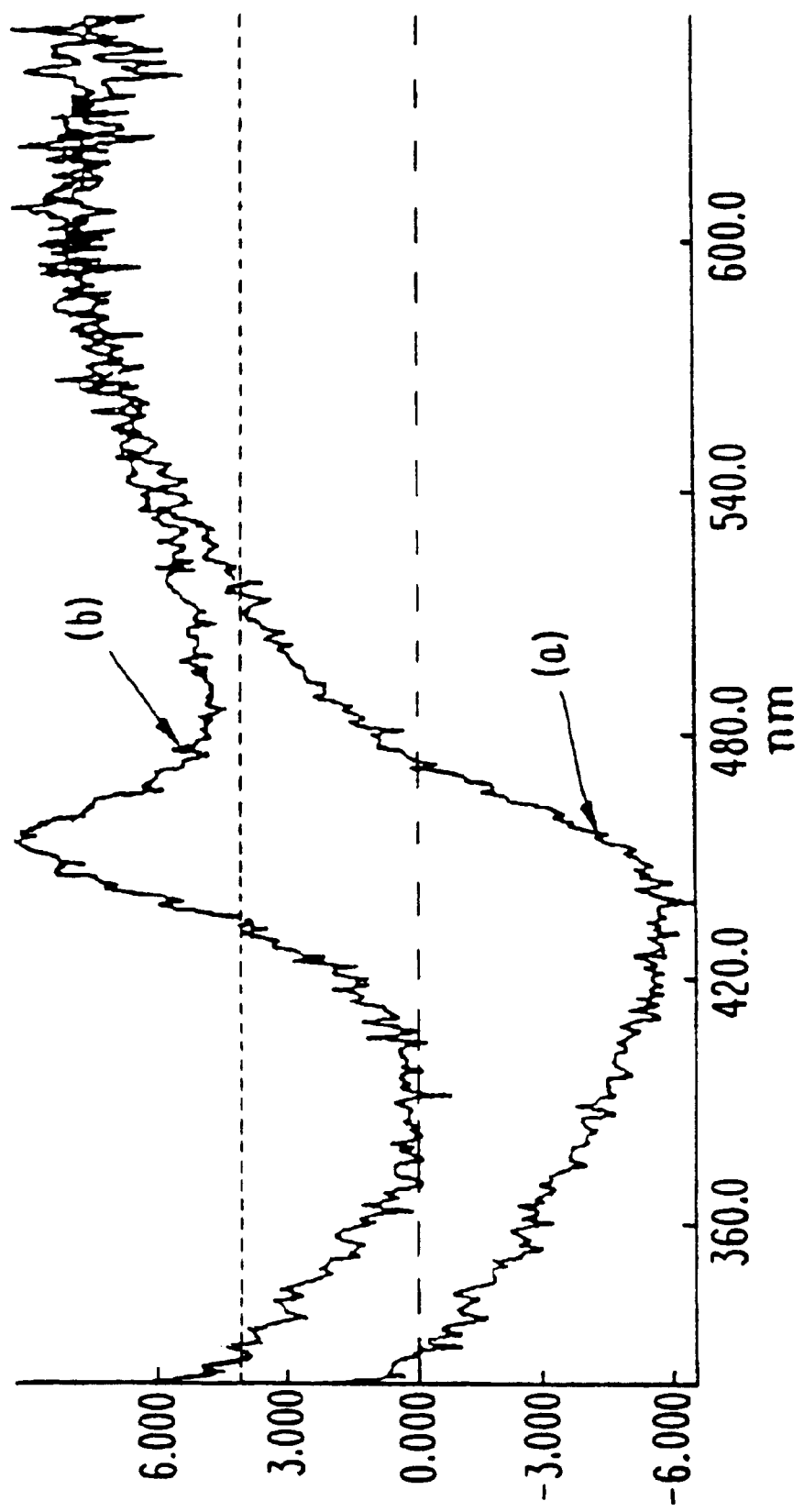
FIG. 6 is (a) the CD spectrum of in situ deposited thin film of polyaniline emeraldine base doped with (1S)-(+) camphor sulfonic acid and (b) the CD spectrum of in situ deposited thin film of polyaniline emeraldine base doped with (1S)-(+) camphor-sulfonic acid, after being subjected to m-cresol vapor treatment.

As shown in FIG. 6, the exposure of the in situ deposited chiral polyaniline thin films to m-cresol vapor resulted in a significant change in the UV/Vis spectra. The initially intense localized polaron peak was replaced by a well-developed free carrier tail in the UV/Vis spectrum. Also, the surface resistance decreased from about $3 \times 10^4$ $\Omega/\square$ to about $1.8 \times 10^3$ $\Omega/\square$. The CD spectrum of the film, after exposure to m-cresol vapor (FIG. 6, line (b)), showed a significant change as compared to the initial CD spectrum before m-cresol vapor treatment (FIG. 6, line (a)). The original negative CD band at about 450 nm became two separated bands—one was a negative CD band at about 400 nm and the other was a positive CD band at about 460 nm. Although not intending to be bound by any theory of operation, it is believed that this change is related to a change in the molecular conformation. These data show that m-cresol induces significant changes in molecular conformation, but that the chirality of the polymer is retained. This is useful for applications to separation processes using different solvent systems.

Example 4

Circular Dichroism Studies of Novel Chiral Polyaniline Solutions

Figure 7:
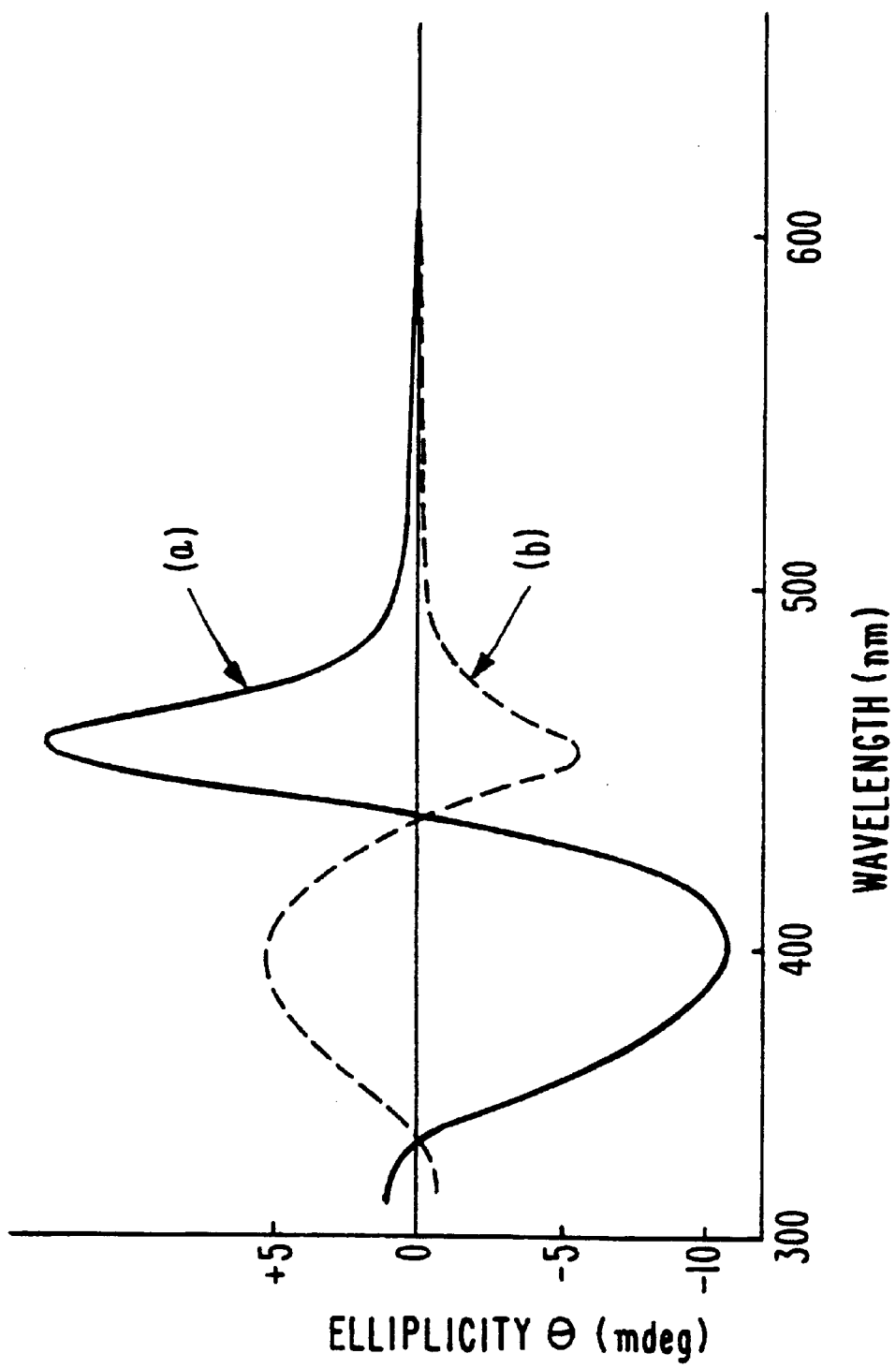
FIG. 7 is (a) the as-synthesized chiral polyaniline powder doped with (+) camphor sulfonic acid in a DMSO solution and (b) the as-synthesized chiral polyaniline powder doped with (−) camphor sulfonic acid in a DMSO solution.
Figure 8:
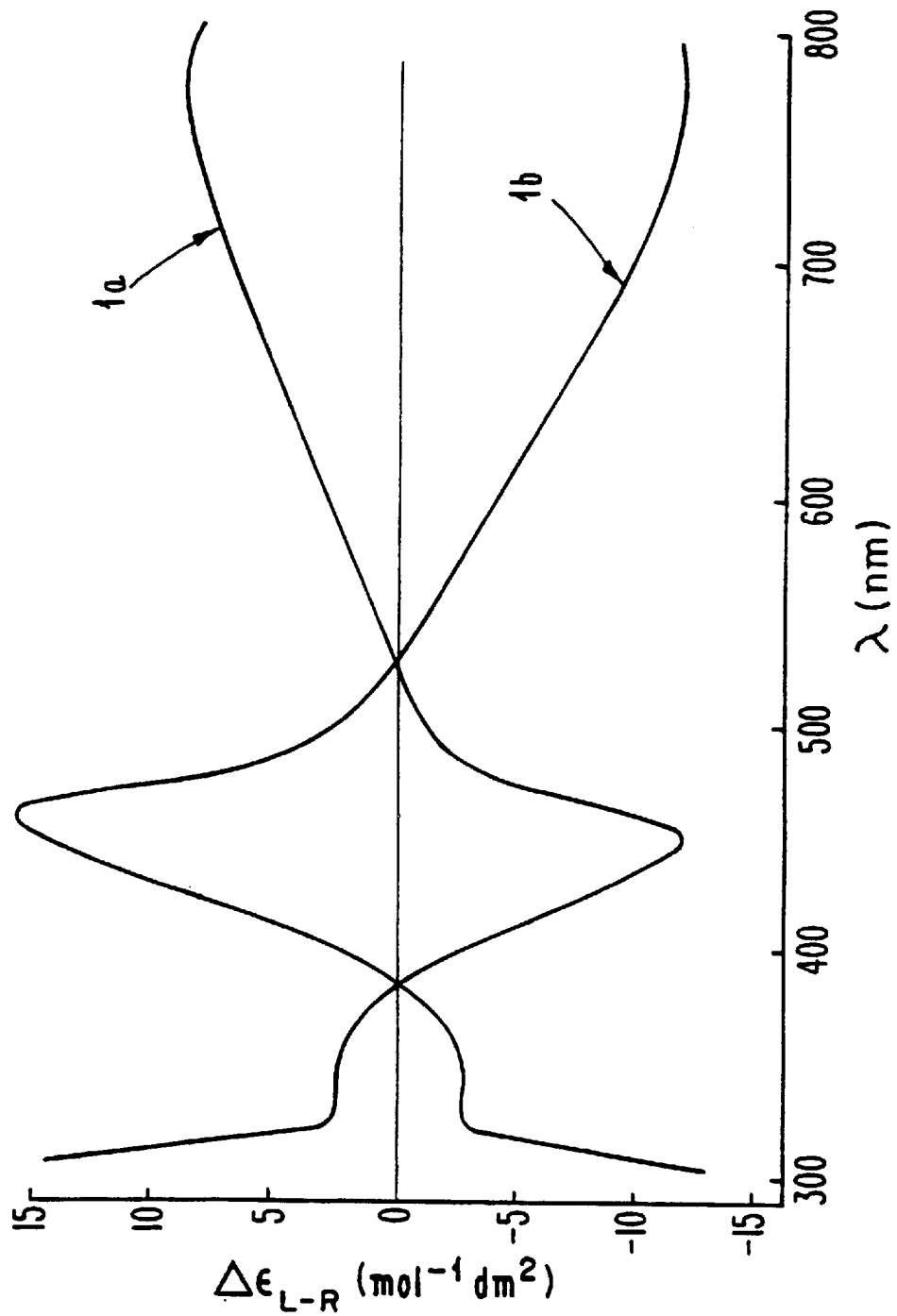
FIG. 8 is the CD spectrum of electrochemically deposited films of polyaniline salt in the emeraldine oxidation state (a) doped with (1S)-(+)-camphor sulfonic acid and (b) doped with (1R)-(−)-camphor sulfonic acid, as described by Majidi et al, supra.

It has been unexpectedly discovered that chemically synthesized chiral polyaniline salt powder doped with a chiral camphor sulfonic acid is very soluble in common organic solvents, such as n-methyl pyrrolidinone (NMP), N,N-dimethyl formamide (DMF), dimethylsulfoxide (DMSO) and $CHCl_3$, thus permitting use of these solutions to process the chiral polymer into films, membranes and fibers. The electrochemically synthesized chiral polyaniline described by Majidi et al, supra, is qualitativley much less soluble in organic solvents as judged by the color of the solution, also, the qualitative relative rate of dissolution of the electrochemically produced form of the polymer is very much less than the rate of dissolution of the chemically synthesized powder of the present invention. Solutions of the (1S)-(+) camphor sulfonic acid dry salt powder in DMSO (FIG. 7(a)) and the (1R)-(−)camphor sulfonic acid dry salt powder in DMSO (FIG. 7(b)) showed a CD absorption band at about 400 nm and a CD band at about 450 nm and. Moreover, the two CD spectra are mirror images of each other. This indicates that the polymer does not lose its chiral properties when it is dissolved in solution.

The disclosure of every patent, patent application and publication cited in the present disclosure is hereby incorporated by reference herein in its entirety.

Although the invention has been set forth in considerable detail, one skilled in the art will appreciate that numerous changes and modifications can be made to the preferred embodiments of the invention and that such changes and modifications may be made without departing from the spirit and scope of the invention.

What is claimed is:

1. A method of synthesizing a chiral polyaniline salt powder comprising:
   reacting an aniline monomer with a chiral dopant acid to produce a first reaction product; and
   mixing the first reaction product with a solution comprising an oxidizing agent and a chiral dopant acid to produce the chiral polyaniline salt powder.

2. The method of claim 1, wherein the oxidizing agent is selected from the group consisting of $FeCl_3 \cdot 6H_2O$, $(NH_4)_2S_2O_8$, $Ce(SO_4)_2$, $KMnO_4$, $KBrO_3$, $K_2Cr_2O_7$, $KIO_3$, $H_2O_2$, $V_2O_5$, $NaVO_3$ and $NaClO$.

3. The method of claim 2, wherein the oxidizing agent is $(NH_4)_2S_2O_8$.

4. The method of claim 1, wherein the chiral dopant acid is selected from the group consisting of (1S)-(+) camphor sulfonic acid, (1R)-(−) camphor sulfonic acid, D-tartaric acid and L-tartaric acid.

5. The method of claim 1, further comprising contacting the chiral polyaniline with a base to convert it to a chiral polyaniline emeraldine base.

6. A method of synthesizing a chiral polyaniline film on a substrate comprising:
   reacting an aniline monomer with a chiral dopant acid to produce a first reaction product;
   immersing a substrate in the first reaction product; and
   mixing the first reaction product with a solution comprising an oxidizing agent and a chiral dopant acid to produce a thin film of the chiral polyaniline salt on the substrate.

7. The method of claim 6, wherein the oxidizing agent is selected from the group consisting of $FeCl_3 \cdot 6H_2O$, $(NH_4)_2S_2O_8$, $Ce(SO_4)_2$, $KMnO_4$, $KBrO_3$, $K_2Cr_2O_7$, $KIO_3$, $H_2O_2$, $V_2O_5$, $NaVO_3$ and $NaClO$.

8. The method of claim 7, wherein the oxidizing agent is $(NH_4)_2S_2O_8$.

9. The method of claim 6, wherein the chiral dopant acid is selected from the group consisting of (1S)-(+) camphor sulfonic acid, (1R)-(−) camphor sulfonic acid, D-tartaric acid and L-tartaric acid.

10. The method of claim 6, wherein the substrate is selected from the group consisting of glass, poly(methyl methacrylate), poly(ethylene phthalate), a silicon wafer and a fabric fiber.

11. The method of claim 6, further comprising contacting the chiral polyaniline with a base to convert it to a chiral polyaniline emeraldine base.

12. A novel chiral polyaniline salt powder produced by a process comprising
   reacting an aniline monomer with a chiral dopant acid to produce a first reaction product; and
   mixing the first reaction product with a solution comprising an oxidizing agent and a chiral dopant acid to produce the chiral polyaniline.

13. The chiral polyaniline of claim 12, wherein the oxidizing agent is selected from the group consisting of $FeCl_3 \cdot 6H_2O$, $(NH_4)_2S_2O_8$, $Ce(SO_4)_2$, $KMnO_4$, $KBrO_3$, $K_2Cr_2O_7$, $KIO_3$, $H_2O_2$, $V_2O_5$, $NaVO_3$ and $NaClO$.

14. The chiral polyaniline of claim 13, wherein the oxidizing agent is $(NH_4)_2S_2O_8$.

15. The chiral polyaniline of claim 12, wherein the chiral dopant acid is selected from the group consisting of (1S)-(+) camphor sulfonic acid, (1R)-(−) camphor sulfonic acid, D-tartaric acid and L-tartaric acid.

16. The chiral polyaniline of claim 12, further comprising contacting the chiral polyaniline salt with a base to convert it to a chiral polyaniline emeraldine base.

* * * * *

UNITED STATES PATENT AND TRADEMARK OFFICE
CERTIFICATE OF CORRECTION

PATENT NO. : 6,090,985  
DATED : July 18, 2000  
INVENTOR(S) : David F. Carmichael et al.

Page 1 of 1

It is certified that error appears in the above-identified patent and that said Letters Patent is hereby corrected as shown below:

Column 39, claim 1,  
Line 65, "AGTTTGCTGG" should read -- AGTTTCGTGG --.

Column 40, claim 1,  
Line 16, "GCACTCCCTG" should read -- GCAGTCCCTG --.

Signed and Sealed this

Twenty-sixth Day of March, 2002

Attest:

Attesting Officer

JAMES E. ROGAN  
Director of the United States Patent and Trademark Office

UNITED STATES PATENT AND TRADEMARK OFFICE
CERTIFICATE OF CORRECTION

PATENT NO.   : 6,090,985
DATED        : July 18, 2000
INVENTOR(S)  : Alan G. MacDiarmid et al.

It is certified that error appears in the above-identified patent and that said Letters Patent is hereby corrected as shown below:

This certicate supersedes Certificate of Correction issued March 26, 2002, the number was erroneously mentioned and should be vacated since no Certificate of Correction was granted.

Signed and Sealed this

Thirtieth Day of March, 2004

JON W. DUDAS
*Acting Director of the United States Patent and Trademark Office*